(12) United States Patent
Saghiri

(10) Patent No.: US 10,905,249 B1
(45) Date of Patent: Feb. 2, 2021

(54) MULTIFUNCTIONAL SMART BEDS AND METHODS OF OPERATING THEREOF

(71) Applicant: Khalid Saghiri, Meknes (MA)

(72) Inventor: Khalid Saghiri, Meknes (MA)

(*) Notice: Subject to any disclaimer, the term of this patent is extended or adjusted under 35 U.S.C. 154(b) by 0 days.

(21) Appl. No.: 16/888,378

(22) Filed: May 29, 2020

(51) Int. Cl.
| | | |
|---|---|---|
| *A47C 31/12* | (2006.01) | |
| *A47C 20/00* | (2006.01) | |
| *A61G 7/015* | (2006.01) | |
| *A61G 7/018* | (2006.01) | |
| *G01G 19/44* | (2006.01) | |
| *A61B 5/00* | (2006.01) | |
| *A61B 5/11* | (2006.01) | |

(52) U.S. Cl.
CPC ........... *A47C 31/123* (2013.01); *A47C 20/00* (2013.01); *A61B 5/1102* (2013.01); *A61B 5/6892* (2013.01); *A61G 7/015* (2013.01); *A61G 7/018* (2013.01); *G01G 19/445* (2013.01); *A61G 2203/10* (2013.01); *A61G 2203/32* (2013.01); *A61G 2203/46* (2013.01); *A61G 2203/70* (2013.01)

(58) Field of Classification Search
CPC ..... A47C 31/123; A47C 20/00; A47C 21/003; A61B 5/1102; A61B 5/6892; A61B 5/117; A61G 7/015; A61G 7/018; A61G 2203/10; A61G 2203/32; A61G 2203/46; A61G 2203/70; G01G 19/445; A47G 2009/006; Y10S 5/904; A61M 21/02; G10L 21/00

See application file for complete search history.

(56) References Cited

U.S. PATENT DOCUMENTS

| | | | | |
|---|---|---|---|---|
| 2008/0005843 A1* | 1/2008 | Lokhorst | ............ | A61G 7/05776 5/655.3 |
| 2011/0118614 A1* | 5/2011 | Brauers | ................. | A61B 5/113 600/500 |
| 2013/0253291 A1* | 9/2013 | Dixon | ................ | A61B 5/14551 600/323 |

(Continued)

OTHER PUBLICATIONS

Krebs, Michael et al., The Adjustment of Physical Properties of Viscoelastic Foam—the Role of Different Raw Materials, American Chemistry Council, 2016; 15 pgs.

*Primary Examiner* — David R Hare
*Assistant Examiner* — Alexis Felix Lopez
(74) *Attorney, Agent, or Firm* — Kwan & Olynick LLP

(57) ABSTRACT

Described herein are multifunctional smart beds and methods of operating thereof. Specifically, a multifunctional smart bed comprises a controller, configured to receive input from various sensors (e.g., load cells positioned in bed legs, thermometers, and/or microphones) and/or user. These inputs are analyzed and used to control various bed components to improve the sleep quality, to monitor users' health, score couple's relationship, and the like. For example, these inputs may be used to control firmness of different mattress portions, change orientations of head, torso, and/or leg sections, adjust the light, and the like. In some examples, the smart bed generates a report indicating one or more sleep duration, sleep depth profile, sleep scope, heart rate, breadth rate, environment conditions, couple's relationship, and the like. Furthermore, in some examples, a multifunctional smart bed is also configured to control external devices in the same environment, e.g., smart switches, smart thermostats.

20 Claims, 8 Drawing Sheets

(56) References Cited

U.S. PATENT DOCUMENTS

| | | | |
|---|---|---|---|
| 2013/0310700 A1* | 11/2013 | Wiard | A61B 5/0402 |
| | | | 600/485 |
| 2014/0325758 A1 | 11/2014 | Mikkelsen et al. | |
| 2015/0334482 A1* | 11/2015 | Rawls-Meehan | H04R 1/028 |
| | | | 381/333 |
| 2016/0234356 A1* | 8/2016 | Thomas | H05K 9/0069 |
| 2017/0135632 A1* | 5/2017 | Franceschetti | A61G 7/002 |
| 2018/0106897 A1* | 4/2018 | Shouldice | A61B 5/1102 |
| 2019/0053761 A1* | 2/2019 | Young | A61B 5/447 |
| 2019/0126000 A1* | 5/2019 | Main | F24F 5/00 |
| 2019/0200777 A1* | 7/2019 | Demirli | A47C 27/082 |
| 2019/0201268 A1* | 7/2019 | Sayadi | G06N 20/00 |
| 2019/0209082 A1* | 7/2019 | Bailey | G16H 40/63 |
| 2020/0060907 A1* | 2/2020 | Childs | G01G 19/52 |
| 2020/0107753 A1* | 4/2020 | Young | G01V 9/00 |
| 2020/0178887 A1* | 6/2020 | Correa Ramirez | A61B 5/4806 |

\* cited by examiner

MULTIFUNCTIONAL SMART BEDS AND METHODS OF OPERATING THEREOF

BACKGROUND

People spend about a third of their lifetime in beds. Multiple studies have shown that the quality and duration of sleep have a major effect on concentration, mental/physical health, and emotional well-being. Furthermore, beds have other uses besides sleep, such as health recovery, intimacy, and general rest (e.g., reading, watching television). Finally, the same bed may be shared by multiple people (e.g., spouses, children) with different sleeping habits and bed requirements (e.g., mattress firmness).

However, modern beds have been lagging behind advances in other technology areas, such as smartphones and smart homes. Conventional beds are still generally limited to flat mattresses. In limited cases, manual adjustment of mattress firmness is available. Specialized beds (e.g., hospital beds) also provide manual adjustment of their head sections (e.g., changing the reclining angle). However, most of these beds are generally limited to manual controls and provide very limited functionality, focused on particular uses of these beds.

What is needed is a multifunctional smart bed, configured to analyze multiple user-related and environment characteristics and provide various operational and reporting options based on the comprehensive analysis of these characteristics.

SUMMARY

Described herein are multifunctional smart beds and methods of operating thereof. Specifically, a multifunctional smart bed comprises a controller, configured to receive input from various sensors (e.g., load cells positioned in bed legs, thermometers, and/or microphones) and/or user. These inputs are analyzed and used to control various bed components to improve the sleep quality, to monitor users' health, score the couple's relationship, and the like. For example, these inputs may be used to control the firmness of different mattress portions, change orientations of the head, torso, and/or leg sections, adjust the light, and the like. In some examples, the smart bed generates a report indicating one or more sleep duration, sleep depth profile, sleep scope, heart rate, breath rate, environment conditions, couple's relationship, and the like. Furthermore, in some examples, a multifunctional smart bed is also configured to control external devices in the same environment, e.g., smart switches, smart thermostats.

In some examples, a multifunctional smart bed comprises a frame, a plurality of legs, each comprising a load cell and coupled to the frame, a mattress, positioned on and supported by a frame, a plurality of environmental sensors, a controller, communicatively coupled to the load cell in each of the plurality of legs and also to each of the plurality of environmental sensors, and a plurality of actuators, communicatively coupled to the controller and configured to change at least one or more bed characteristics of the multifunctional smart bed based input from the controller. For example, the one or more bed characteristics comprise at least one of mattress firmness and one or more positions of different sections of the frame relative to each other.

In some examples, the plurality of actuators is configured to adjust one or more environment characteristics of the environment around the multifunctional smart bed based input from the controller. For example, the one or more environment characteristics comprise at least one of the light around the multifunctional smart bed, sound around of the multifunctional smart bed, temperature around the multifunctional smart bed, humidity around the multifunctional smart bed, or air quality around the multifunctional smart bed.

In some examples, the controller is configured to determine presence of one or more users in the multifunctional smart bed based on input from the load cell in each of the plurality of legs. More specifically, the controller is further configured to determine identity of the one or more users in the multifunctional smart bed. For example, the controller comprises a sound classifier, configured to determine the identity of the one or more users in the multifunctional smart bed. In some examples, the identity of the one or more users in the multifunctional smart bed is determined based on input from the load cell in each of the plurality of legs.

In some examples, the multifunctional smart bed further comprises a ballistocardiogram belt, communicatively coupled to the controller and configured to determine at least one of a heart rate, a respiration rate, or tossing rate of the one or more users in the multifunctional smart bed, wherein the controller is configured to match at least one of the heart rate, the respiration rate, or the tossing rate of the user identity of the one or more users in the multifunctional smart bed.

In some examples, the plurality of environmental sensors comprises multiple microphones to differentiate snoring of multiple users of the multifunctional smart bed. For example, the plurality of environmental sensors comprises one or more microphones, configured to distort an actual sound, obtained around the multifunctional smart bed thereby generating a distorted sound, not recognizable for a human.

In some examples, the controller receives the distorted sound from the one or more microphones and does not have access to the actual sound. For example, the controller is configured to identify one or more the following sound categories in the distorted sound: a normal conversation, laughing and joyous conversation, arguing and shouting, and intimate acts. For example, the controller is configured to collectively analyze the one or more identified sound categories together input from the load cell in each of the plurality of legs. In some examples, the controller is configured to score an intimate relationship based on at least the distorted sound.

Also provided is a method of operating a multifunctional smart bed. In some examples, the method comprises receiving data from load cells in legs of the multifunctional smart bed, processing the data, received from the load cells, using a controller of the multifunctional smart bed, and adjusting at least one or more bed characteristics of the multifunctional smart bed using a plurality of actuators of the multifunctional smart bed based input from the controller.

In some examples, the method further comprises obtaining actual sound around the multifunctional smart bed using one or more microphones of the multifunctional smart bed and, using the one or more microphones, distorting the actual sound thereby generating distorted sound. The method further comprises providing the distorted sound to the controller of the multifunctional smart bed. For example, the one or more microphones isolate the controller of the multifunctional smart bed from the actual sound around the multifunctional smart bed. In some examples, the data, received from the load cells, is processed by the controller together with the distorted sound to generate the input for adjusting the at least one or more bed characteristics of the multifunctional smart bed.

In some examples, the method further comprises obtaining ballistocardiogram data from a ballistocardiogram belt of the multifunctional smart bed, wherein the data, received from the load cells, is processed by the controller together with the ballistocardiogram data to generate the input for adjusting the at least one or more bed characteristics of the multifunctional smart bed

DETAILED DESCRIPTION

Figure 1A:
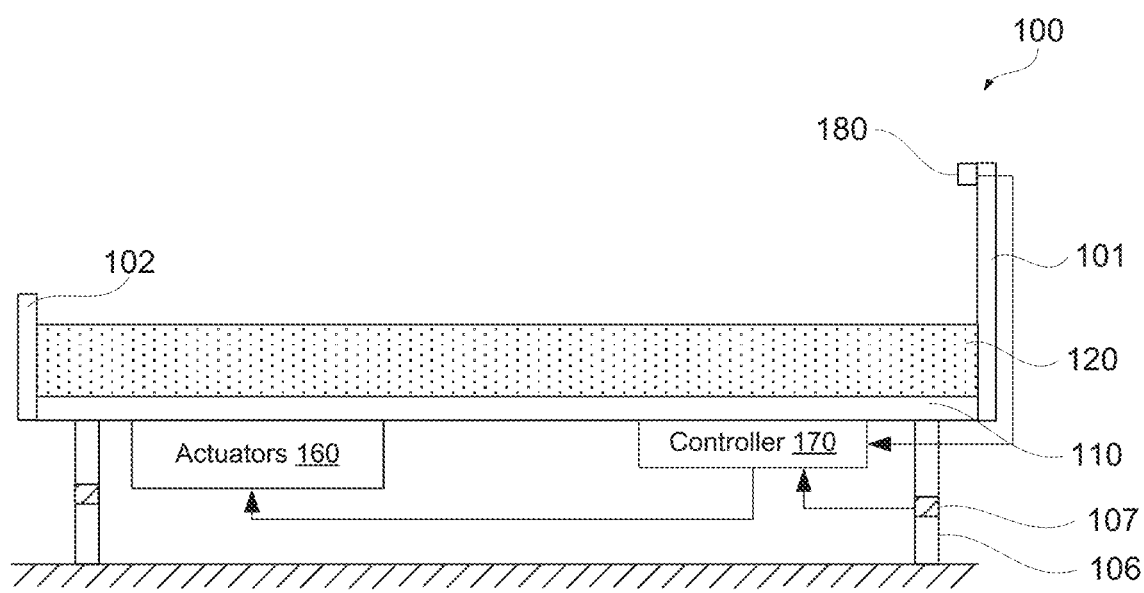
FIG. 1A is a schematic side view of a multifunctional smart bed, in accordance with some examples.

In the following description, numerous specific details are set forth in order to provide a thorough understanding of the presented concepts. In some examples, the presented concepts are practiced without some or all of these specific details. In other instances, well known process operations have not been described in detail so as to not unnecessarily obscure the described concepts. While some concepts will be described in conjunction with the specific examples, it will be understood that these examples are not intended to be limiting.

INTRODUCTION

Multifunctional smart beds and methods of operating thereof provide various novel functions, which are not available from conventional beds. Some examples of these functions include, but are not limited to, health monitoring, sleep management, mattress hardness adjustments, and intimacy features. These functions are provided in an automated manner using various sensors and actuators of the smart beds. In some examples, the users' input is minimal or not present at all.

In some examples, a smart bed is equipped with load cells, which are coupled to or integrated into legs of the smart bed. Each load cell continuously measures the weight applied to the corresponding leg, which allows to monitor changes in users' weight (e.g., weight gains/losses), weight distribution (e.g., movements while in bed, position in the bed), times of entering and leaving the bed (e.g., waking up at night), and the like. The weight data is provided to a controller, which aggregates and analyzes this data for various characteristics. For example, a data analysis may be used to generate reports for the users (e.g., weight profile, sleep profile) and/or control various actuators of the smart bed (e.g., changing the orientation of different frame portions, changing the hardness of different mattress portions, turning on/off the light).

In some examples, the smart bed controller comprises various modules, specifically configured to provide various functions of the smart bed. For example, the controller may include an environmental module, configured to receive input from environmental sensors (e.g., microphones, light sensors, thermometers) and to control environment adjusters (e.g., speakers, lights, heaters). The environmental module is also configured to interact with one or more other modules of the controller.

Another module example is a mattress hardness module, which is configured to control and adjust the mattress hardness or, more specifically, the hardness of different mattress portions. Yet another example of the controller modules is a health monitoring module, which is configured to receive input from various sensors, including specific health sensors, such as a ballistocardiogram (BCG) belt. The health monitoring module is configured to provide reports to users about their expected health conditions (e.g., weight profile, sleep efficiency, heart rate (HR), respiration rate (RR), tossing rate (TR) and the like).

In some examples, the smart bed controller comprises a sleep management module, which receives sensor data and output from other modules related to the sleep quality. The sleep management module is also configured to control various actuators, e.g., to improve the quality of sleep. For example, the sleep management module may adjust the light, temperature, and/or the sound of the bed environment. In some examples, the sleep management module instructs the mattress hardness module to adjust the hardness of one or more sections of the mattress.

In some examples, the smart bed controller comprises an intimacy module, which is configured to receive and analyze pre-filtered data from one or more sensors, such as microphones or load cells. Pre-filtering of sensors data before this data is analyzed and stored allows addressing various privacy concerns. For example, a sound modifier is used at the microphone level to remove certain types of sounds and/or to make various and, in some examples, even all sounds unrecognizable to humans (for privacy). However, the modified sound still retains enough distinctive and/or discriminating information allowing the sound classification algorithm to carry out various operations, such as multi-speaker separation, voice recognition, sentiment analysis, and the like. In other words, instead of removing parts of the sound, the sound is modified/distorted in one or more ways to make the modified sound unrecognizable to humans. The modified sound still contains distinctive features for the artificial intelligence (AI) classifier to differentiate between the different classes of sound. The overall content of the sound is lost during the sound modification while various essential differentiating features are retained. It should be noted that the sound modification is irreversible for privacy reasons. As such, the modified sound cannot be converted back into the original sound. The irreversible functionality is achieved by processing the original sound using an irreversible mathematical function. As a result, the modified sound can be stored and shared without concerns to the privacy.

Smart Bed Examples

FIG. 1A is a schematic side view of smart bed 100, in accordance with some examples. Smart bed 100 is also referred to as a multifunction smart bed, due to various novel functions described below. Smart bed 100 comprises frame 110 and mattress 120, supported by frame 110. Smart bed 100 also comprises plurality of legs 106, such that each plurality of legs 106 comprises or is coupled to load cell 107. Plurality of legs 106 keeps frame 110 and mattress 120 above the floor level.

Load cells 107 are configured to measure the weight applied to each of legs 106. The output of load cells 107 may be used to determine various weight changes associated with the use of smart bed 100 (e.g., a user entering or leaving smart bed 100), weight distribution of smart bed 100. In some examples, these weight measurements and analysis are performed continuously, which allows determining dynamic changes in users' weight, movements while in bed (e.g., measuring changes in weight distribution). Overall, load cells 107 enable determining when a person lays in the bed, leaves the bed, moves while in the bed, and the like. The output of load cells 107 is provided to and used by controller 170.

Smart bed 100 also comprises controller 170, which is configured to receive input from various sensors (e.g., environmental sensors 180, load cells 107) and to provide instructions to actuators 160. Specifically, controller 170 is communicatively coupled to load cell 107 in each of plurality of legs 106 and to each environmental sensor 180. Actuators 160 are also communicatively coupled to controller 170 and configured to change one or more bed characteristics of multifunctional smart bed 100, based input from controller 170. Additional features of controller 170 are described below with reference to FIG. 2 and FIG. 7.

Figure 1B:
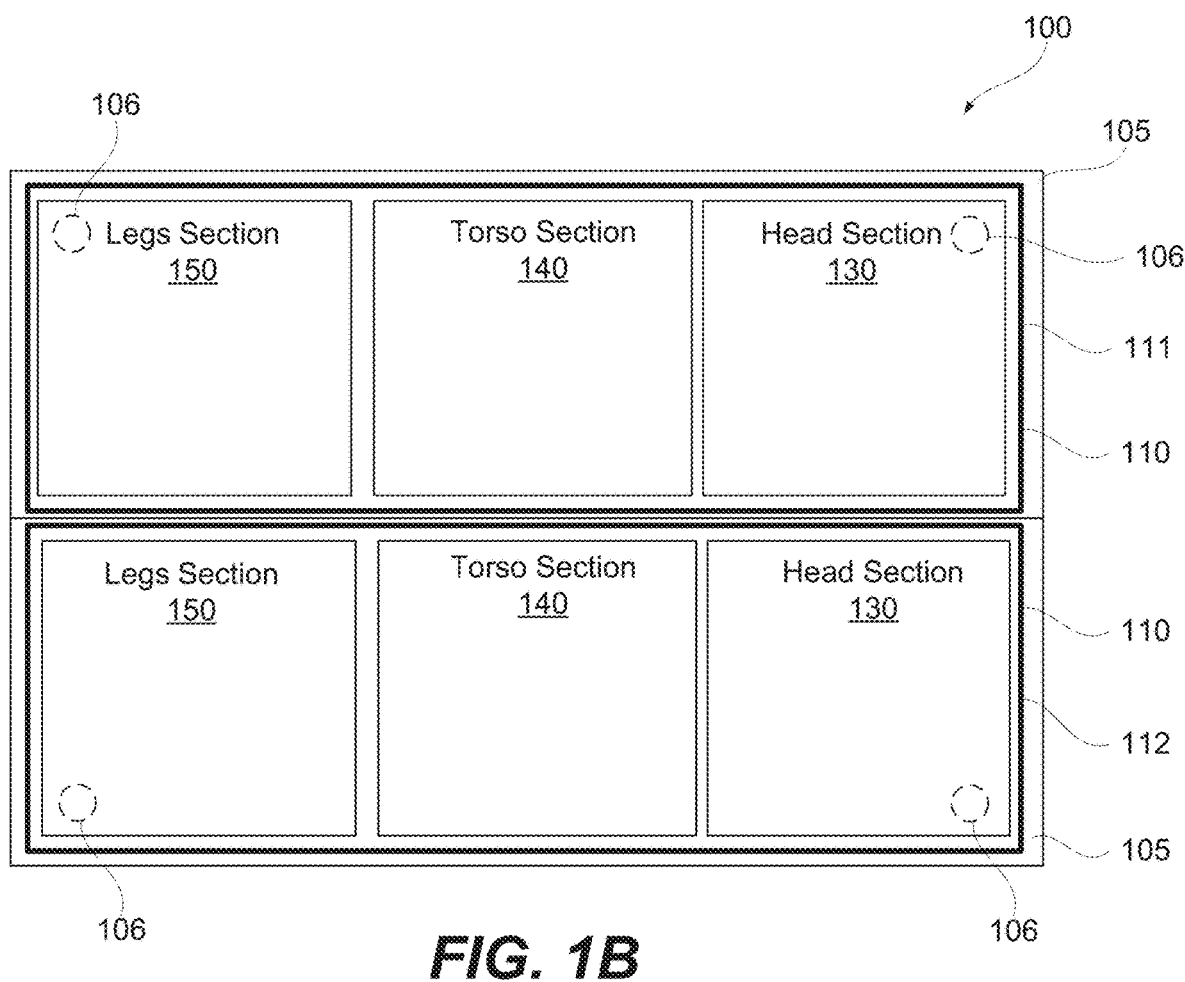
FIG. 1B is a schematic top view of the multifunctional smart bed of FIG. 1A with the mattress removed, in accordance with some examples.

FIG. 1B is a schematic top view of smart bed 100, in accordance with some examples. In these examples, smart bed 100 comprises two frames 110, e.g., first frame 111 and second frame 112. In other examples, smart bed 100 comprises only one frame 110 or comprises one or more additional frames 110 (e.g., a third frame). Plurality of legs 106 provides support to both first frame 111 and second frame 112. For example, smart bed 100 further comprises one or more bases 105, providing support to each of first frame 111 and second frame 112 and acting an intermediate structure between each of first frame 111 and second frame 112 and plurality of legs 106. For example, each of first frame 111 and second frame 112 has a dedicated base 105 and is adjustably coupled to this base 105.

Figure 1C:
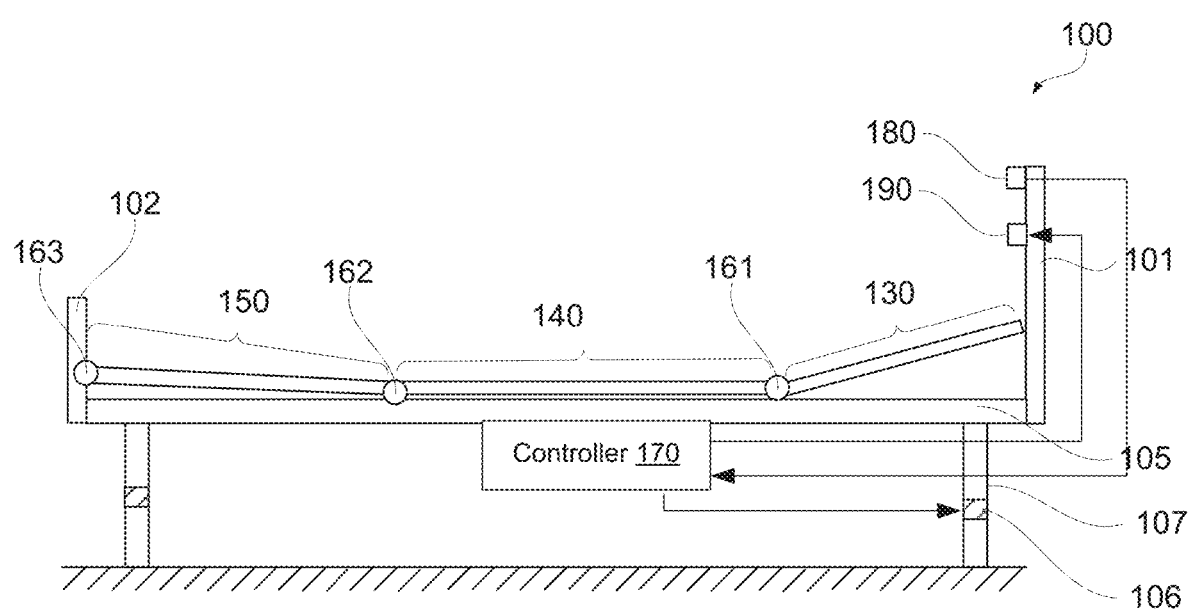
FIG. 1C is a schematic perspective view of one frame of the multifunctional smart bed of F 1A, in accordance with some examples.

In some examples, each frame is adjustably coupled to base 105. Specifically, each of first frame 111 and second frame 112 comprises multiple sections, which are independently movable, e.g., relative to base 105 and/or plurality of legs 106. Referring to FIGS. 1B and 1C, each of first frame 111 and second frame 112 comprises head section 130, torso section 140, and legs section 150. Various examples with fewer or more sections are also within the scope. Head section 130, torso section 140, and legs section 150 in each frame are independently adjustable from each other (in the same frame and from corresponding sections in another frame). For example, head section 130 of first frame 111 is independently adjustable from head section 130 of second frame 112. These adjustments may involve an angle of the corresponding section relative to base 105 and/or relative to one or more other sections, which may be referred to as reclining angles. Different adjustments of each section and reasons for these adjustments are described below.

In some examples, smart bed 100 comprises plurality of actuators 160. One example of actuators is drives used, e.g., for changing the orientation of at least one of head section 130, torso section 140, and/or legs section 150 relative to base 105. FIG. 1C illustrates an example of smart bed 100 comprising first drive 161 for changing the orientation of head section 130, second drive 162 for changing the orientation of torso section 140, and third drive 163 for changing the orientation of legs section 150. Each drive is independently controlled by controller 170. Besides mechanical actuators, such as drives, actuators 160 may be other types such as actuators for adjusting the environment, which may be referred to as environment adjusters 190, which are described below.

Referring to FIG. 1A, in some examples, smart bed 100 also comprises plurality of environmental sensors 180. Various components of smart bed 100 may be used to support environmental sensors 180, such as frame 110, headboard 101, footboard 102, and the like. In more specific examples, at least one or more of environmental sensors 180 are positioned on headboard 101, e.g., at the highest possible position of headboard 101. In general, the position of environmental sensors 180 depends on the type of sensing. For example, microphones may be placed on opposite sides of headboard 101 (e.g., one on the right and one on the left) to ensure the sound differentiation of different people in smart bed 100. Furthermore, even the same sensor may be placed at multiple different locations, e.g., a microphone in headboard 101, while the sound processing circuitry at another location.

Environmental sensors 180 are configured to measure the temperature, humidity, air quality, atmospheric pressure, light level, noise level, and/or other characteristics in the environment surrounding smart bed 100. Environmental sensors 180 may be positioned at various locations relative to frame 110 and/or mattress 120. In the same or other examples, environmental sensors 180 comprise one or more thermometers, e.g., positioned at various height levels or portions of the bed to determine the temperature distribution in the bed environment. It should be noted that smart bed 100 may comprise various other sensors, focusing on user parameters, which are further described below. Another example of environmental sensors 180 is a light sensor, configured to detect the intensity of the light in the bed environment. The output of environmental sensors 180 is provided to controller 170.

In some examples, environmental sensors 180 are positioned proximate or attached to head section 130, e.g., positioned in headboard 101. For example, environmental sensors 180 comprise a microphone for measuring both ambient noise and the noise produced by a person in smart bed 100 (e.g., snoring). In more specific examples, environmental sensors 180 comprises two microphones, each positioned in headboard 101. As such, one microphone is used from one person (e.g., positioned over first frame 111), while the other microphone is used to capture sounds from another person (e.g., positioned over second frame 112). This type of arrangement is used, e.g., to detect which of two people is actually snoring.

In some examples, smart bed 100 comprises one or more environment adjusters 190, which are specific examples of actuators 160. Environment adjusters 190 may be configured to adjust the temperature, humidity, light level, noise level, and/or other characteristics in the environment surrounding smart bed 100. Some examples of environment adjusters 190 include, but are not limited to, heaters, fans, humidifiers, lights, speakers, and the like. Environment adjusters 190 are controlled based on input from controller 170. For example, controller 170 may instruct environment adjusters 190 to change one or more environmental parameters based on input from environmental sensors 180 and/or determinations made by one or more modules of controller 170, which are described below.

Figure 2:
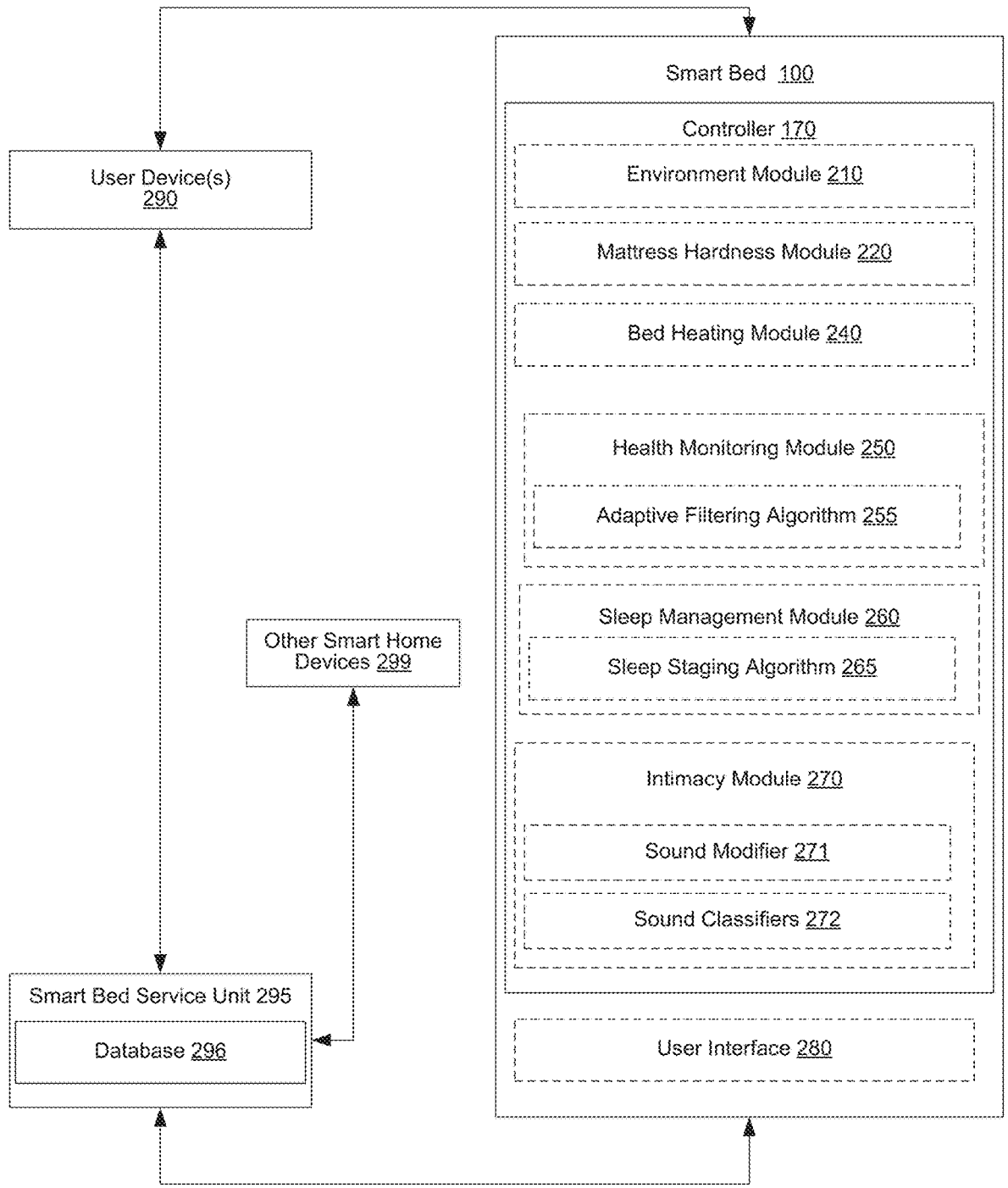
FIG. 2 is a schematic block diagram of various components of the multifunctional smart bed, in accordance with some examples.

Referring to FIG. 2, smart bed 100 is communicatively coupled to one or more user devices 290 and/or smart bed service unit 295. Some examples of user devices 290 include, but are not limited to, a smartphone, smartwatch, tablet computer, laptop computer, desktop computer, smart home centers/hubs, and the like. User devices 290 may be communicatively coupled to smart bed 100 either directly, e.g., via Bluetooth protocol, or indirectly, e.g., via local and/or global networks (Wi-Fi, Internet). Controller 170 is configured to deliver to user devices 290 various sensor and other like data, obtaining by controller 170. In some examples, controller 170 is configured to generate reports based on this data, and the reports are provided to user devices 290. Furthermore, controller 170 is configured to receive various inputs from user devices 290, e.g., to change various settings of smart bed 100.

In some examples, smart bed service unit 295 is a backend remote server, communicatively coupled to smart bed 100 via at least global networks (e.g., Internet). For example, smart bed service unit 295 is a server hosted by a manufacturer of smart bed 100 to obtain data about various operating conditions of smart bed 100, e.g., to initiate a service/repair call, update functionality (e.g., over the air updates), and the like. In some examples, database 296 stores various settings for smart bed 100, which are automatically downloaded and used by smart bed 100 and, in some examples, other devices around smart bed 100, e.g., smart home devices 299. Furthermore, in some examples, smart bed service unit 295 develops settings for smart bed 100, based on input from multiple other smart beds, thereby performing data mining and analysis. Finally, smart bed service unit 295 may upload settings for a specific user when this user travels and sleeps in other smart beds, e.g., hotel, hospital, a second home, and the like.

Bed Controller Examples

As shown in FIG. 2, controller 170 of smart bed 100 comprises various modules, configured to provide various functions of smart bed 100. Some examples of these modules are environment module 210, mattress hardness module 220, bed heating module 240, health monitoring module 250, sleep management module 260, and intimacy module 270. One having ordinary skill in the art would understand that controller 170 may have fewer modules and/or additional modules, enabling various functions described in this disclosure. These modules may be enabled in hardware and/or software as further described below with reference to FIG. 7.

Referring to FIG. 2, in some examples, controller 170 also comprises user interface 280, which may be used by a user (e.g., while the user is in smart bed 100) to control various functions of smart bed 100 and/or view various data, gathered by controller 170. Some functions of user interface 280 are the same as of user devices 290, described above. In other words, a person may use either user device 290 or user interface 280 to control smart bed 100 and review various data. In some examples, user interface 280 comprises a dedicated set of input devices (e.g., switches, dials) for controlling specific functions of smart bed 100. In the same or other examples, user interface 280 comprises a reconfigurable touchscreen. For example, a user may manually set various characteristics of smart bed 100 through user interface 280. These manually-set characteristics may be combined with automatically-determined characteristics (by various modules of controller 170, described above). For example, manually-set characteristics may be used to override the automatically-determined characteristics or further adjust automatically-determined characteristics. Some examples of manually-set characteristics include, but are not limited to, the color of the lights, its intensity, music sound level, speed of the position adjusting motors, and the like.

Environment Module Examples

In some examples, controller 170 comprises environment module 210. Environment module 210 is configured to receive data related to the environment surrounding smart bed 100, e.g., from environmental sensors 180. This type of data may be referred to as bed environment data and may include temperature, humidity, noise, and the like. Environment module 210 is configured to selectively share this bed environment data with other modules, such as with sleep management module 260. For example, sleep management module 260 is configured to correlate the bed environment data with the user sleep quality, which may be presented as a sleep score. The functionality of sleep management module 260 is described below.

In some examples, environment module 210 controls environment adjusters 190 and/or other smart home devices 299 to achieve desired environment characteristics, e.g., determined by environment module 210 or other modules. For example, environment module 210 may determine the desired environment characteristics based on the current setting (provided by the user), historic trends (e.g., learned settings), the identity of the user (e.g., determined from the weight, sound profile), and/or other like factors.

In some examples, environment module 210 is configured to control the noise level around smart bed 100 or, more specifically, around the head portion of each user. For example, environment adjusters 190 may include one or more speakers or headphones controlled by environment module 210 to generate specific sound (e.g., mood setting sounds, relaxation, meditation), white noise, noise cancellation, and the like.

In some examples, the sound data received by environment module 210 represent a modified/distorted version of the actual sound in the environment, to ensure user privacy. The distortion may be performed by analog hardware, e.g., an analog circuitry in environment module 210. Processing of the modified/distorted sound (e.g., sound classification) is described below with reference to FIG. 6.

In some examples, controller 170 uses a sound input for controlling firmness units 400. For example, smart bed 100 with two frames may have two microphones. The two microphones are used to detect the snoring person, by comparing the amplitude of the sound in both microphones. This comparison allows determining, which side the snoring person is at. In some examples, the snoring sound is detected by a supervised learning convolutional neural network (CNN) artificial intelligence (AI) model, trained to differentiate snoring from non-snoring sounds. In some examples, the sound signal is altered at the receiving hardware level, e.g., a microphone, to protect the user's privacy.

In some examples, environment module 210 is configured to control the light level around smart bed 100 or, more specifically, around each user. For example, environment module 210 may receive a signal from load cells 107 indicating that a user is getting up from the bed. In this case, environment module 210 instructs a light to turn on to assist the user with navigating the environment around smart bed 100.

In some examples, if one or more environment conditions cannot be controlled by environment adjusters 190, then environment module 210 provides a report (to a user), recommending various adjustments to the environment, e.g., installing sound insulation solutions in the bedroom, moving smart bed 100 to a new location, closing the shutters. As described below, in some examples, smart bed 100 is communicatively coupled to other smart home devices 299, such as smart thermostats, smart lights, smart shutters, and the like. In these examples, the output of environment adjusters 190 is used for controlling one or more of these devices, without a direct involvement of the user.

Overall, environment module 210 is configured to receive and process various types of environment data (temperature, humidity, noise, etc.) and, in some examples, to correlate this data with other types of data (e.g., sleep quality, health conditions, activities, and the like). Environment module 210 is configured to determine target environment parameters and to control environment adjusters 190 and/or external components responsible for maintaining the environment around smart bed 100. In some examples, environment module 210 is configured to generate a report, related to the environment conditions and recommendations for changing these environment conditions, and to send this report to user device 290.

Environment module 210 is configured to determined target environment parameters and to control environment adjusters 190 and/or external components responsible for maintaining the environment around smart bed 100. In some examples, environment module 210 is configured to generate a report, related to environment conditions and recommendations for changing these environment conditions, and to send this report to user device 290.

Bed Heating Module Examples

In some examples, controller 170 comprises bed heating module 240. Bed heating module 240 is used to control the power applied to each of one or more heating blankets, heating pillows, heating bedsheets, and/or heating mattresses of smart bed 100, e.g., based on various inputs received by controller 170 and/or based on various determinations by controller 170. The mattress heating should be distinguished from adjusting mattress firmness, using one heating elements embedded into the mattress, as further described below.

In some examples, operations of bed heating module 240 are synchronized with operations of environment module 210, which may control the temperature of the environments. For example, bed heating module 240 may turn on the heating blanket when environment module 210 allows for the ambient temperature to go down.

Examples of Adjusting Mattress Hardness

In some examples, controller 170 comprises mattress hardness module 220. Mattress hardness module 220 is used to control and adjust the hardness of mattress 120, e.g., based on input from sensors or other modules, e.g., sleep management module 260, environment module 210, and the like. For example, sleep management module 260 may be configured to automatically adjust the hardness of mattress 120 to improve the overall sleep quality, e.g., represented by the sleep score as further described below. In some examples, mattress hardness module 220 is used to control the hardness of different portions of mattress 120, as will now be described with reference to FIG. 4.

Figure 4:
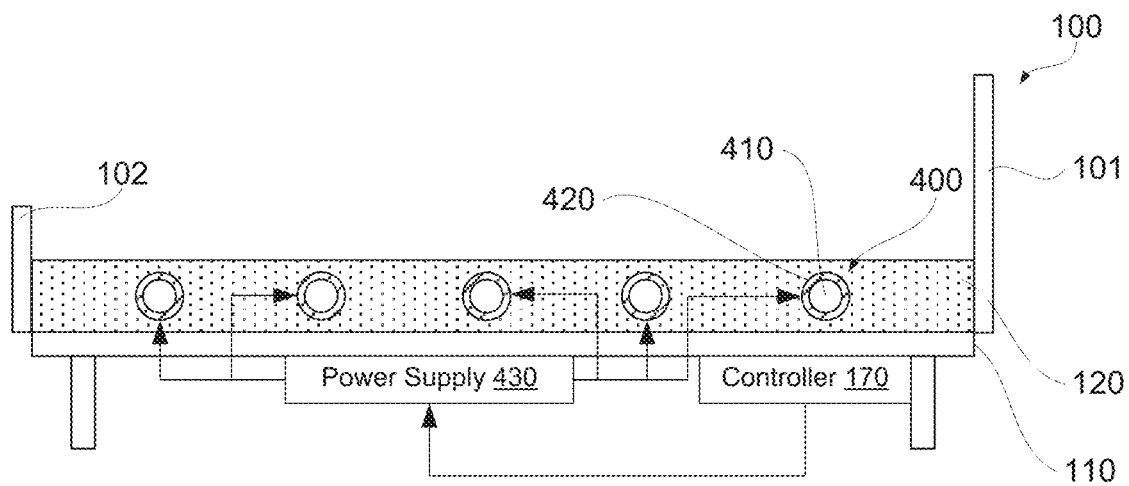
FIG. 4 is a schematic side view of a multifunctional smart bed, illustrating multiple mattress firmness units distributed throughout the mattress of the multifunctional smart bed, in accordance with some examples.

FIG. 4 is a schematic cross-sectional view of smart bed 100, showing multiple firmness units 400, integrated into mattress 120. Each firmness unit 400 comprises viscoelastic foam base 410 and heating unit 420. In some examples, heating unit 420 is configured as a jacket/shell surrounding viscoelastic foam base 410. Heating unit 420 may be an electrical resistance heater, with temperature level controlled by mattress hardness module 220 or, more generally, by controller 170.

Viscoelastic foam base 410 is formed from viscoelastic polyurethane foam with a tailored formulation. Below a certain foam set temperature (related to the glass transition temperature of the viscoelastic polyurethane foam), viscoelastic foam base 410 has a set hardness level. As the temperate of viscoelastic foam base 410 increases due to heating by heating unit 420 and exceeds the foam set temperature, the hardness of viscoelastic foam base 410 decreases.

For purposes of this disclosure, the glass transition is defined as a temperature range, during which the polymer goes over from a hard and glassy state to a soft and rubbery material. Unlike the melting temperature (which is a thermodynamic property of solid material), the glass transition temperature is a dynamic property of amorphous polymers and is related to relaxation behavior of local polymer chain segments. As a result, the glass transition temperature depends on the following factors affecting the mobility of polymer chain segments:

(1) cross-link density in the network structure, (2) aromaticity (e.g., defines as a weight fraction of aromatic structures in the polymer matrix), (3) plasticizer concentration, and other like factors.

In some examples, the glass transition temperature of the viscoelastic polyurethane foam forming viscoelastic foam base 410 is between +25° C. to +40° C. This temperature is much higher than conventionally used. Such a high glass transition temperature is achieved by (1) increasing the crosslink density by increasing the isocyanates to polyol ratio (referred to as an "index"), (2) varying the chemical composition of network segments by varying the chain lengths of the polyols and monomers, and (3) increasing the urea and poly-urea content of the foam by increasing the water content of the formulation.

In some examples, the viscoelastic polyurethane foam is formed using a tightly closed container where the foam is reacted. The resulting carbon dioxide ($CO_2$) gas generated from the reaction is prevented from escaping the closed container but in a controlled manner. Specifically, the generated gas inside the closed container exerts a homogeneously distributed mechanical force that works against foam expansion and therefore prevents density decrease. The less the gas escaping the foaming chamber the higher the density. The higher the gas permitted to escape by a controller valve the lower is the density. This new foaming method allows the production of a high density viscoelastic polyurethane foam, with a high poly-urea content while still keeping a high density which in some examples ranges between 35 $kg/m^3$ and 75 $kg/m^3$ or higher. In some examples, the density is between 55 $kg/m^3$ and 65 $kg/m^3$ to sustain high load bearings and high deformations especially during the heated mode during which the foam is exhibiting its soft properties and therefore is more prone to deformation. Furthermore, the foam has a high poly-urea content due the high level of water content in the formulation.

In some examples, the foam is foamed in a multitude of mold shapes to give the desired shape. Furthermore, in some examples, the foam is machined (e.g., using a computer numerical control (CNC) machining tool) to the desired shape from a starting block. The cut foam bun is then inserted into an electrically heated jacket having several heating elements in the interior side of the jacket adjacent to the foam bun and a heat insulating material (e.g., aluminum foil) on the exterior side in order to prevent heat energy loss and also to prevent the components that would come in contact with the device from being heated.

In some examples, multiple firmness units 400 are positioned into the same mattress 120 and, more specifically, distributed along the length of mattress 120. For example, a pair of adjacent firmness units 400 may be spaced apart between 200 millimeters and 500 millimeters. The cross-sectional size (e.g., diameter of each firmness unit 400) may be between 50 millimeters and 300 millimeters.

Each of these multiple firmness units 400 is independently controlled by controller 170. More specifically, controller 170 may provide input to power supply 430, individually coupled to each of firmness unit 400. Various shapes of firmness unit 400 or, more specifically, of viscoelastic foam base 410 are within the scope, such as cylindrical, rectangular, triangular, and the like.

In some examples, controller 170 uses a sound input for controlling firmness units 400. For example, smart bed 100 with two frames may have two microphones, one in head section 130 of each frame. The two microphones are used to detect the snoring person, by comparing the amplitude of the sound in both microphones. This comparison allows determining, which side the snoring person is at. In some examples, the snoring sound is detected by a supervised learning convolutional neural network (CNN) artificial intelligence (AI) model, trained to differentiate snoring from non-snoring sounds. In some examples, the sound signal is altered at the receiving hardware level, e.g., a microphone, to protect the user's privacy.

Furthermore, in some examples, upon detecting the snoring, controller 170 instructs one or more drives to change the position of one or more of head section 130, torso section 140, and leg section 150. Referring to FIG. 1C, in specific examples, controller 170 instructs first drive 161 to increase the angle of head section 130, relative to the ground, thereby raising the sleeper's head position. The change in head position is known to stop the snoring temporarily because the breathing airways blocked by the relaxed larynx muscles get cleared by the change of position of the head. Each time the snoring is resumed the head position is moved again, at slow speed (e.g., at less than 5° per minute) to avoid waking up the sleeping person. For example, raising user's head about 20° to 30° from the horizontal plane opens the nasal airway passages and may prevent snoring. Another cause of snoring may be uneven weight distribution.

Health Monitoring Examples

Figure 3:
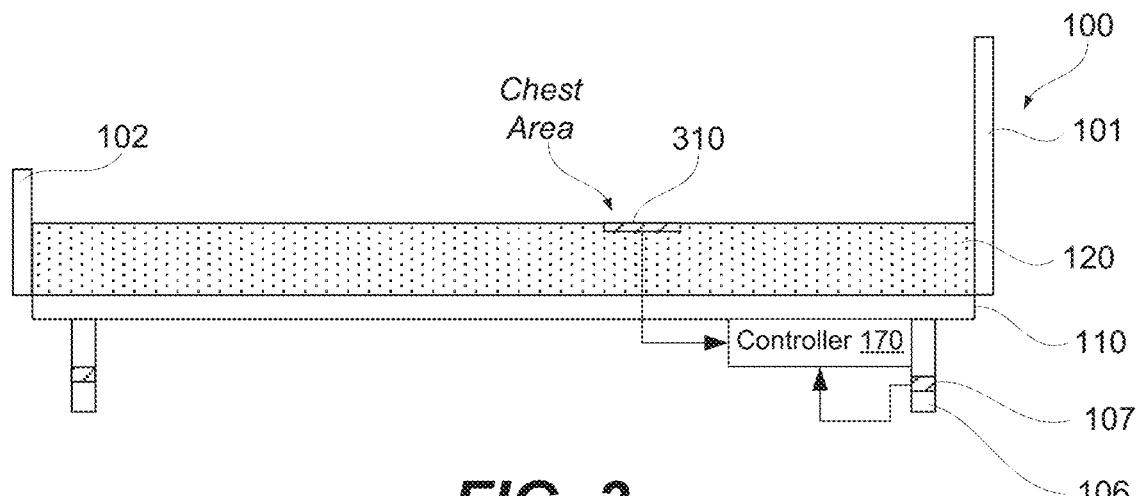
FIG. 3 is a schematic side view of a multifunctional smart bed, illustrating a ballistocardiogram (BCG) belt, embedded into the mattress of the multifunctional smart bed, in accordance with some examples.

Referring to FIG. 2, in some examples, controller 170 also includes health monitoring module 250. Furthermore, referring to FIG. 3, smart bed 100 comprises one or more BCG belts 310, attached to or integrated into controller mattress 120. Controller 170 or, more specifically, health monitoring module 250 receives input from BCG belts 310 and, in some examples, from load cells 107, provided in legs 106 of smart bed 100. Specifically, load cells 107 provide continuous and nonintrusive monitoring of person's weight. For example, a person does not need to specifically use the scale, which is often forgotten. Such continuous weight monitoring is particularly important for people having undiagnosed heart and hypertension issues as they often are not able to notice weight gain due to body water retention, which is considered an important signal for cardiovascular malfunctions. Continuous weight monitoring may provide various trending, day-to-day comparison (e.g., overeating on a particular day). For example, smart bed 100 is able to perform day-to-day comparison for the same time of the day, which is one of the major recommendations for keeping a good record of weight. Furthermore, smart bed 100 is able to detect early stages of obesity, when the weight control is relative easy, in comparison to later stages. At the same time, detecting weight gain is harder at this early stage because of the unnoticeable small and gradual increase of weight. Smart bed 100 overcomes this challenge using continuous and consistent monitoring.

This weighting feature of smart bed 100 is self-calibrating. Specifically, controller 170 of smart bed 100 or, more specifically, health monitoring module 250 comprises an algorithm that allows accurate weight measurements without being impacted by different configurations of smart bed 100, e.g., like adding/removing various objects from smart bed 100, e.g., pillows or blankets. Specifically, load cells 107 continuously monitor the weight in conjunction with continuous monitoring of the user presence in smart bed 100, e.g., using BCG signal, noise sensing, movement sensor, etc. In other words, controller 170 is not misled by non-living objects being added/removed from smart bed 100. Furthermore, controller 170 is configured to recognize different users using the same smart bed 100 (e.g., family members). For example, controller 170 uses sound input (e.g., from a microphone in environmental sensors 180), previous weight data, and the like to differentiate users.

In some examples, BCG belts 310 are used to monitor the user's Heart Rate (HR), monitor the user's Respiration Rate (RR), and/or monitor the Tossing Rate during sleep (TR). For example, BCG belts 310 comprise polyvinylidenefluorid (PVDF) transducers.

It should be noted that the difficulty of extracting the HR and/or RR information from the BCG signal is primarily due to various interferences of other movement signals and noise signals with the HR and RR signals. As a result, conventional systems that are limited to one type of BCG sensors, such as PVDF transducers, electromechanical films (EMFi), or load cells are limited in their accuracy.

Unlike conventional systems, smart bed 100 allows combining input from BCG belts 310 and load cells 107. Furthermore, health monitoring module 250 comprises adaptive filtering algorithm 255, various function of which will now be described in more detail. BCG belts 310 are used to detect raw BCG signals, while load cells 107 are used to detect user's movements, while in smart bed 100. For example, the sensitivity of load cells 107 is lowered. Adaptive filtering algorithm 255 subtracts various noises, e.g., associated with user's movements in smart bed 100, potential movements of smart bed 100, and the like (detected by load cells 107) from the raw BCG signal (obtained using BCG belts 310). The processed BCG signal, produced by adaptive filtering algorithm 255 is more accurate than the raw BCG signal from BCG belts 310.

Furthermore, continuous and prolonged monitoring of various BCG signals, described above, is highly beneficial in comparison with infrequent measurements conventionally associated with these types of signals. For example, this continuous monitoring helps to improve the diagnosis and monitoring of various heart and respiration related dysfunctions, such as tachycardia, bradycardia, apnea, tachypnea, and bradypnea. In some examples, the recording of the body movements by load cells 107 also help with the diagnosis and monitoring of the restless legs syndrome (RLS) since health monitoring module 250 is configured to differentiate various origins of the body movements, e.g., load cells 107 positioned closer to leg section 150 vs. load cells 107 positioned closer to torso section 140. As noted above, these analyses are carried out in a continuous and non-invasive way without any required actions by the user, Sleep Management Examples Referring to FIG. 2, in some examples, controller 170 also includes sleep management module 260. Sleep management module 260 is configured to interact and share data with one or more other modules in controller 170. For example, sleep management module 260 is configured to receive HR, RR and TR data from health monitoring module 250. In the same or other examples, sleep management module 260 is configured to receive sound, temperature, humidity, and other like data from environment module 210. More specifically, sleep management module 260 is configured to identify snoring from the sound data, e.g., obtained by microphones positioned around head section 130. In some examples, the snoring detection algorithm determined if the snoring sound coincides with the inspiration (inhalation, during which the snoring occurs) based on the respiration signal, extracted from the BCG signal. As such the accuracy of snoring classification is greatly increased in comparison to conventional sound classifiers. The detection of snoring may be important for the diagnosis of obstructive sleep apnea, which causes a person to temporarily stop breathing during the sleep and raises the risk for diabetes, obesity, hypertension, heart attack, and other cardiovascular problems.

In some examples, sleep management module 260 controls operation of one or more drives, for adjusting the orientation of one or more of head section 130, torso section 140, and/or legs section 150 relative to the respective frame. Furthermore, in some examples, sleep management module 260 is configured to send instructions to bed heating module 240, e.g., to adjust the temperature of one or more heating blankets.

In some examples, sleep management module 260 comprises and employs sleep staging algorithm 265, which identifies particular sleep stages (e.g., an awaken stage, a light sleep stage, a mid-sleep stage, and a deep sleep stage) and associated parameters (e.g., duration, sequence, tossing rate, leaving bed, and start-end times). Sleep management module 260 uses these parameters to establish a sleep score. For example, the max perfect sleep is assigned a score of 100%. Points are subtracted for each event with negative effects on the sleep quality, such as tossing, tachypnea, too much time before falling asleep, going later than recommended time. For example, getting out of bed multiple times during may drop the sleep score by 10%, determining restless sleep (e.g., excessing turning in bed)—by 4%, going to bed later than a regular window—by 8%, not being able to fall asleep during a preset period of time—by 2%, detecting tachypnea—by 2%. In the example where all such conditions are present, the total decrease is 26%, bringing the score down to 74%. Overall, each event is associated with an "importance coefficient", which determined the number of points subtracted this for this event. These coefficients can be tailored to specific users based on various factors associated with the user, e.g., age, gender, health condition.

In some examples, sleep management module 260 generates a "sleep curve", which is a time profile identifying different sleep states (e.g., awake, light sleep, mid-level sleep, and deep sleep). Similarly, in some examples, sleep management module 260 generates a sleep score curve, which combines sleep scores for a set period of time (e.g., a week, a month, etc.). The sleep curve may be presented in a report provided to the user. In some examples, the report also indicates the percentage of time corresponding to each sleep state.

In some examples, the sleep score is correlated with the environmental parameters, recorded during the same period. As noted above, some examples of these parameters include temperature, humidity, noise level, and luminosity level. Sleep management module 260 is configured to provide reports and make recommendations for adjusting one or more environmental parameters, e.g., to improve the sleep score/quality of the sleep. Furthermore, in some examples, sleep management module 260 collects data containing sleep scores at different environmental conditions, compares the sleep scores at varying environmental parameters, establishes a correlation between the sleep scope and environmental parameters, and recommends various environmental parameters for improving the sleep score.

In some examples, the sleep score is also used as a feedback data for adjusting various parameters of smart bed 100, such as the orientation of one or more head section 130, torso section 140, and leg section 150 relative to the corresponding frame and/or firmness of mattress 120. Various features for hardness adjustments are described below. Other examples of parameters that may be adjusted include, but are not limited to, light, sound, room temperature, and humidity, e.g., produced by environment adjusters 190, Examples of Intimacy Features Obtaining information using various environmental sensors 180 raises some privacy concerns. For example, beds are used for intimate moments, and people may not want various data (audio, weight changes, etc.) being recorded and shared externally, e.g., to smart bed service unit 295. To address these privacy concerns, smart bed 110 includes various features both on the hardware level and the software level. For example, a microphone of environmental sensors 180 is equipped with a special information-losing filter, limiting the types of sounds captured by the microphone and transmitted to controller 170. It should be noted that the information losing feature is implemented in the microphones electronic circuitry. For example, signals from two microphones are supplied to an analog circuit that performs mathematical operations on the signals, before this analog signal is converted into a digital signal (e.g., by an analog to digital converter) and transmitted to controller 170. The purpose of the mathematical operations performed is to 'lose information' from the signal that are important for human ear recognition of the sound content but are not important for the AI model's sound classification task that may be performed later, e.g., by sound classifier 272 of controller 170. As such, the audio signal is altered before the signal is even converted into a digital signal, which enhances privacy and precludes information loss if system's security is breached.

Furthermore, referring to FIG. 2, in some examples, controller 170 comprises intimacy module 270. Intimacy module 270, in turn, comprises sound modifier 271, which eliminates any intimacy-classified sounds from the recorded audio stream. Specifically, sound modifier 271 is configured to identify or at least differentiate between the following categories: (1) a normal conversation, (2) laughing and joyous conversation, (3) arguing and shouting, and (4) sex related sounds. In some examples, the same mathematical operations, described above in the context of analog circuitry, are used to modify the sound files in AI model training. As such, the AI model is capable of differentiating and classifying the desired categories of sounds.

These features allow smart bed 100 to capture audio from the bed environment without gathering any private information (such as speech content, intimate sounds, and the like). Controller 170 only stores and process the classification categories, listed above. All other events that are of no interest to our system are not picked up or understood.

In some examples, the output from load cells 107 is also used as a source of information about potential intimate acts. The force profile (over time) recorded by load cells 107 corresponding to intimate acts is distinct from other activities in smart bed 100. This output may be used to supplement determination of one of the four categories listed above by sound modifier 271. In other words, sound modifier 271 uses a combination of sounds and the force signals to determine the correct classification. For examples, the output received from load cells 107 may be used to determine the intensity, duration, and time of various activities.

Furthermore, the information from load cells 107 provides information on whether the couple started to separate their sleeping places, which can be used as an indicator of a negative evolution of the marital relationship.

In some examples, intimacy module 270 is used as a communication medium between the partners by setting up the aroma diffuser, music, and the lighting of the room to a particular setup that can signal some given message to the other partner. This can even be set automatically if the couple chooses to let the system surprise them with actions of its own when it notices that the relationship score needs some boosting or if it notices through the sound system that the mood is ripe for some fun. In some examples, intimacy module 270 is configured to control an aroma diffuser, provided in environment adjusters 190. For example, intimacy module 270 may instruct the aroma diffuser to infuse a scent around smart bed 100, upon detection of intimate activities in smart bed 100. In some examples, intimacy module 270 is configured to control a speaker, provided in environment adjusters 190. For example, intimacy module 270 may instruct the speaker to play selected sounds (e.g., melody, song, etc.), upon detection of intimate activities in smart bed 100. In some examples, intimacy module 270 is configured to control a light, provided in environment adjusters 190. For example, intimacy module 270 may instruct the light (e.g., an LED strip) to change intensity (e.g., dim), color, and the like upon detection of intimate activities in smart bed 100.

In some examples, intimacy module 270 is configured to score an intimate relationship based on at least the distorted sound. More specifically, other sensor inputs (e.g., the load cells) are used. For examples, the score may be established over time and based the sex frequency, separate-sleeping frequency, percentage of time having fun in bed vs. time spent arguing and shouting, percentage of time spent sleeping in a hugging or very close position vs sleeping in the same bed but distantly (e.g., using the load cells), and information about each person's position in the bed. In some examples, the score and the trend are shared with the users of smart bed 100 or even shared with a couple's therapist (e.g., based on specific permission from the users). Overall, intimacy module 270 is configured to provide objective evidence about the evolution of the relationship, in comparison to the subjective accounts conventionally provided by each party during a therapy session.

Examples of Operating Multifunctional Smart Beds

Figure 5:
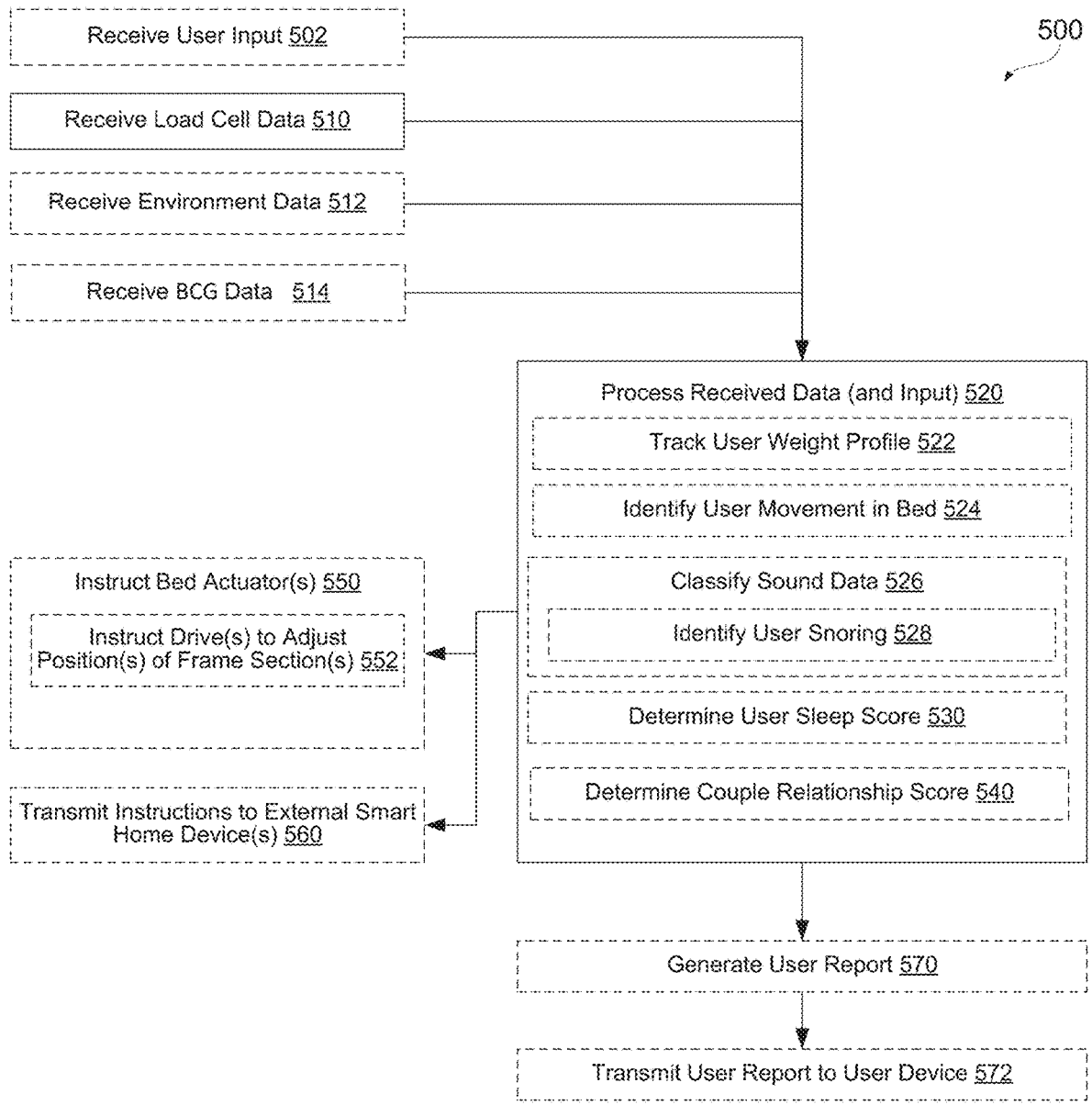
FIG. 5 is a process flowchart corresponding to a method of operating a multifunctional smart bed, in accordance with some embodiments.

FIG. 5 is a process flowchart corresponding to method 500 of operating smart bed 100, in accordance with some examples.

Method 500 may involve receiving user input (block 502). The user may provide input via user interface 280 of controller 170 and/or user device 290, which is communicatively coupled to smart bed 100. Some examples of the user input include, e.g., mattress hardness, sound selection, light selection, heating blanket temperature, and the like.

Method 500 may involve receiving load cell data (block 510). The load cell data represent weight at each leg of smart bed 100. This data may be gathered continuously and is used, e.g., to determine when the user got into the bed, left the bed, turning in the bed, overall weight monitoring of the user, and the like.

Method 500 may involve receiving environmental data (block 512). Various examples of the environment data are described below, e.g., ambient temperature, light, noise, humidity, air quality. This data is used by controller 170, e.g., to determine effect of the environment on the sleep quality.

Method 500 may involve receiving BCG data (block 514). For example, the BCG data may be received from BCG belt 310, installed into mattress 120 as, e.g., described above with reference to FIG. 3.

Method 500 may involve receiving and processing the received data and input (block 520). Various types of data processing are within the scope, such as tracking the user weight profile (block 522), identifying user movements in bed (block 524), classifying sound data (block 526) such as to identify snoring (block 528) and to determine user's sleep score (block 530) and couple relationship score (block 540).

Method 500 may involve instructing one or more bed actuators (block 550) to perform various functions, such as adjusting positions of one or more sections of the frame (block 552).

Method 500 may involve transmitting instructions to external smart home devices (block 560). For example, controller 170 may send instructions to a smart thermostat to adjust the temperature of the environment around the bed.

Method 500 may involve generating a user report (block 570) and transmitting this report to user devices (block 572).

Figure 6:
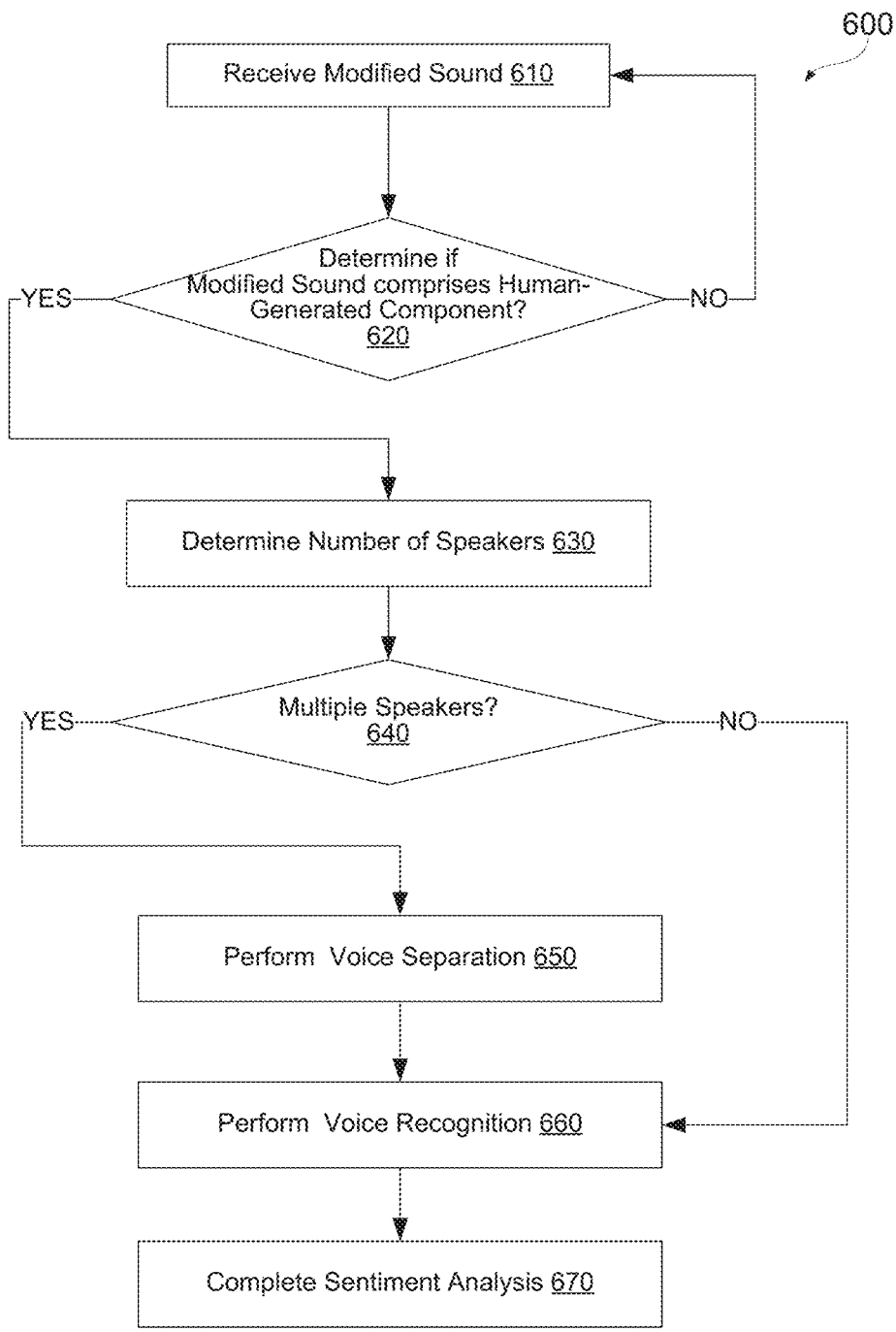
FIG. 6 is a process flowchart corresponding to a method for classification of modified sound, in accordance with some examples.

FIG. 6 is a process flowchart corresponding to method 600 for user identification and sound classification. Method 600 uses modified/distorted sound as input, to ensure privacy, and received (block 610) from smart bed 100. As such, method 600 may be executed by a system, which is remote to but connect to smart bed 100. In some examples, method 600 comprises determining (decision block 620) if the modified sound is human related sound, e.g., to differentiate the modified sound from silence or other non-human sounds (e.g., sounds from the street, ventilation system sounds, and the like). Once the modified sound is identified as human, method 600 proceeds with determining (block 630) if the modified sound corresponds to one or multiple speakers. If there are multiple speakers (decision block 640), then method 600 proceeds with performing (block 650) voice separation by individual speakers. Method 600 then proceeds with voice recognition (block 660) to allocate different audio portions to each speaker. Method 600 then proceeds with a sentiment analysis (block 670) where the modified sound (separated by each individual speaker) is classified into one or more of the following categories: snoring, normal conversation, joyous conversation, shouting, fighting conversation, and intimate sounds. In some examples, the speaker recognition is implemented by asking a user to pronounce a given sentence in his/her smart phone microphone or using microphones in smart bed 110. A trained AI model extracts a voice print from this audio and uses it to recognize the user's voice. In the case of a two person bed two audios are collected.

Computer System Examples

Figure 7:
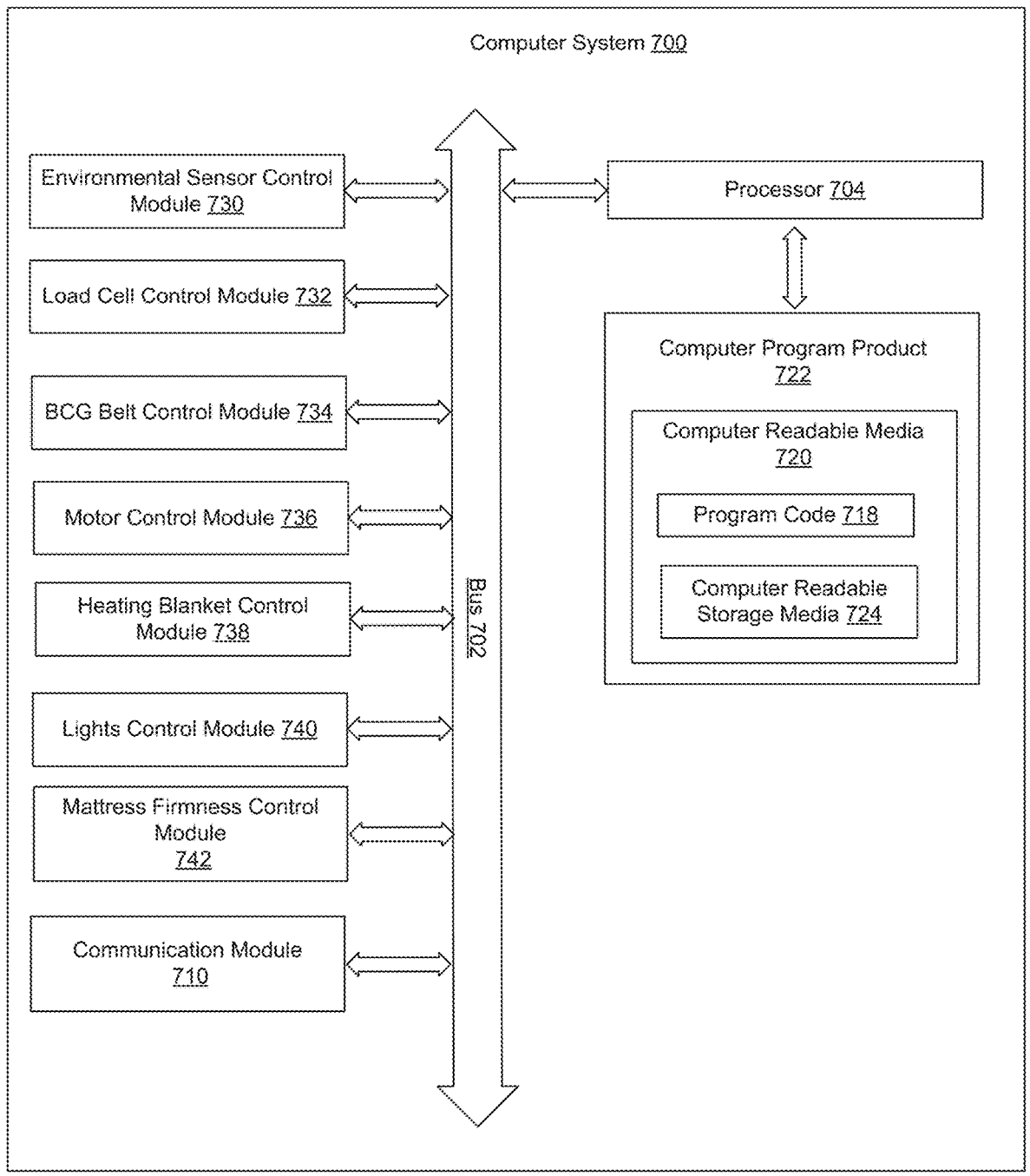
FIG. 7 is a block diagram of the controller of the multifunctional smart bed, in accordance with some examples.

FIG. 7 is a block diagram corresponding to computer system 700 and computer program product 722, which are used to support and implement various functions of smart bed 100 described above. Specifically, various components of smart bed 100 (e.g., controller 170) are implementable as and supportable by components of computer system 700 and computer program product 722, e.g., hardware and/or software modules. In some examples, computer system 700 comprises bus 702, which provides communications between processor 704 and various modules. Processor 704 is configured to execute instructions for software (e.g., computer program product 722).

Various processes of smart bed 100 are performed by processor 704 using computer-implemented instructions. These instructions are referred to as program code 718, computer usable program code, or computer readable program code that is read and executed by a processor in processor 704. Program code in different examples is embodied on different physical or computer readable storage media Program code 718 is located in a functional form on computer readable media 720 that is selectively removable and is loaded onto or transferred to computer system 700 for execution by processor 704. Program code 718 and computer readable media 720 form or provide computer program product 722 in these illustrative examples. In one example, computer readable media 720 is or includes computer readable storage media 724. In these illustrative examples, computer readable storage media 724 is a physical or tangible storage device used to store program code 718 rather than a medium that propagates or transmits program code 718.

Computer system 700 comprises one or more modules, designed to implement various functions of smart bed 100. For example, computer system 700 comprises environmental sensor control module 730, which receives and processes (e.g., pre-processes/partially processes) input from environmental sensors 180. In some examples, computer system 700 comprises load cell control module 732, which receives and processes (e.g., pre-processes/partially processes) input from load cells 107. In some examples, computer system 700 comprises BCG belt control module 734, which receives and processes (e.g., pre-processes/partially processes) input from BCG belt 310. In some examples, computer system 700 comprises motor control module 736, which provides input to drive 161, drive 162, and/or drive 163. Furthermore, motor control module 736 may receive various inputs, such as the position of each section of smart bed 100. In some examples, computer system 700 comprises heating blanket control module 738, which provides input to a heating blanket. Furthermore, heating blanket control module 738 may receive various inputs, such as the temperature of the environment, the temperature of the blanket, the temperature of viscoelastic foam bases 410 in mattress. In some examples, computer system 700 comprises lights control module 740, which provides input to lights or, more generally, to environment adjusters 190. In some examples, computer system 700 also comprises mattress firmness control module 742, which provides input to heating units 420 of mattress 120. Computer system 700 also comprises communications unit 710, which provides communications with other computer systems or devices, such as user devices 290 and/or smart bed service unite 295. For example, communications unit 710 is a network interface card, Bluetooth module, and the like.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatus. Accordingly, the present examples are to be considered as illustrative and not restrictive.

What is claimed is:

1. A multifunctional smart bed comprising:
   a frame, comprising multiple sections, independently movable relative to each other;
   a plurality of legs, each comprising a load cell and coupled to the frame;
   a mattress, positioned on and supported by the frame;
   a plurality of environmental sensors, comprising one or more microphones, configured to obtain an actual sound from around the multifunctional smart bed, and to distort the actual sound thereby irreversibly generating a distorted sound using an irreversible mathematical function, implemented in software or hardware,
      wherein the distorted sound comprises distinctive features for differentiating between different sounds categories;
   a controller, communicatively coupled to and configured to receive and process input from the load cell in each of the plurality of legs and to each of the plurality of environmental sensors; and
   a plurality of actuators, communicatively coupled to the controller, mechanically coupled to the frame, and configured to change at least one or more bed characteristics of the multifunctional smart bed based input from the controller.

2. The multifunctional smart bed of claim 1, wherein the one or more bed characteristics comprise at least one of mattress firmness or positions of the multiple sections of the frame relative to each other.

3. The multifunctional smart bed of claim 1, wherein the plurality of actuators is configured to adjust one or more environment characteristics of an environment, around the multifunctional smart bed, based on input from the controller.

4. The multifunctional smart bed of claim 3, wherein the one or more environment characteristics comprise at least one of light around of the multifunctional smart bed, sound around of the multifunctional smart bed, temperature around of the multifunctional smart bed, humidity around the multifunctional smart bed, or air quality around the multifunctional smart bed.

5. The multifunctional smart bed of claim 1, wherein the controller is configured to determine presence of one or more users in the multifunctional smart bed, based on the input from the load cell in each of the plurality of legs.

6. The multifunctional smart bed of claim 5, wherein the controller is further configured to determine an identity of each of the one or more users in the multifunctional smart bed.

7. The multifunctional smart bed of claim 6, wherein the controller comprises a sound classifier, configured to determine the identity of the one or more users in the multifunctional smart bed.

8. The multifunctional smart bed of claim 6, wherein the identity of each of the one or more users in the multifunctional smart bed is determined based on the input from the load cell in each of the plurality of legs.

9. The multifunctional smart bed of claim 6, further comprising a ballistocardiogram belt, communicatively coupled to the controller and configured to determine at least one of a heart rate, a respiration rate, or a tossing rate of the one or more users in the multifunctional smart bed, wherein the controller is configured to match at least one of the heart rate, the respiration rate, or the tossing rate to a user identity of each of the one or more users in the multifunctional smart bed.

10. The multifunctional smart bed of claim 1, wherein the plurality of environmental sensors comprises multiple microphones, configured to differentiate snoring of multiple users of the multifunctional smart bed.

11. The multifunctional smart bed of claim 1, wherein the controller receives the distorted sound from the one or more microphones and does not have access to the actual sound.

12. The multifunctional smart bed of claim 1, wherein the controller is configured to score an intimate relationship based on at least the distorted sound.

13. The multifunctional smart bed of claim 1, wherein the controller is configured to identify one or more of the sound categories in the distorted sound, the sound categories are selected from the group consisting of a normal conversation, laughing and joyous conversation, arguing and shouting, and intimate acts.

14. The multifunctional smart bed of claim 13, wherein the controller is configured to collectively analyze the one or more identified sound categories together with input from the load cell in each of the plurality of legs.

15. A method of operating a multifunctional smart bed, the method comprising:
obtaining an actual sound around the multifunctional smart bed using one or more microphones of the multifunctional smart bed;
using the one or more microphones, distorting the actual sound thereby irreversibly generating a distorted sound using an irreversible mathematical function, implemented in software or hardware,
wherein the distorted sound comprises distinctive features for differentiating between different sounds categories; and
providing the distorted sound to a controller of the multifunctional smart bed.

16. The method of claim 15, wherein the one or more microphones isolate the controller of the multifunctional smart bed from the actual sound around the multifunctional smart bed.

17. The method of claim 15, further comprising receiving data from load cells in each of a plurality of legs of the multifunctional smart bed, the plurality of legs supporting a frame of the multifunctional smart bed,
wherein the data, received from the load cells, is processed by the controller together with the distorted sound to generate an input for adjusting at least one or more bed characteristics of the multifunctional smart bed.

18. The method of claim 17, further comprising obtaining ballistocardiogram data from a ballistocardiogram belt of the multifunctional smart bed, wherein the data, received from the load cells, is processed by the controller together with the ballistocardiogram data to generate the input for adjusting the at least one or more bed characteristics of the multifunctional smart bed.

19. The method of claim 15, further comprising identifying, at the controller, one or more of the sound categories in the distorted sound, the sound categories are selected from the group consisting of a normal conversation, laughing and joyous conversation, arguing and shouting, and intimate acts.

20. The method of claim 15, further comprising analyzing the distorted sound, at the controller, for at least one of a multi-speaker separation, a voice recognition, or a sentiment analysis.

* * * * *